US00PP11426P

United States Patent [19]

Cosner et al.

[11] Patent Number: Plant 11,426

[45] Date of Patent: Jun. 20, 2000

[54] IMPATIENS PLANT NAMED 'DEEP PURPLE'

[76] Inventors: Harlan Brian Cosner; Sue Lynn Cosner, both of P.O. Box 173, Broadbent, Oreg. 97414

[21] Appl. No.: 09/088,445

[22] Filed: Jun. 1, 1998

[51] Int. Cl.[7] ..... A01H 5/00

[52] U.S. Cl. ..... Plt./317

[58] Field of Search ..... Plt./317

[56] References Cited

U.S. PATENT DOCUMENTS

P.P. 8,359 8/1993 Cole ..... Plt./317

*Primary Examiner*—Howard J. Locker

*Assistant Examiner*—Kent L. Bell

[57] ABSTRACT

A new and distinct cultivar of Impatiens plant named 'Deep Purple', characterized by it's large, deep purple flowers which are held above or beyond the foliage; consistently double and symmetrical flower form; numerous flowers per plant; freely and continuously flowering; freely branching, dense growth habit; upright mounded plant habit, globular to triangular in shape; and dark green foliage with reddish blotches on the underside.

3 Drawing Sheets

The invention described in this application is a new and distinct cultivar of double flowered Impatiens plant, botanically known as *Impatiens walleriana,* which shall be hereinafter referred to by its cultivar name of 'Deep Purple'.

The new cultivar is a seedling of unknown parentage discovered growing in our Coquille, Oreg., breeding area. It was found among a group of seedlings from random crosses made by us in our breeding program. The new cultivar was discovered on Aug. 12, 1995. Asexual reproduction of the cultivar by lateral stem cuttings at Coquille, Oreg., has shown the uniqueness of this new cultivar to be stable, and that it reproduces true to type in successive generations of asexual reproduction.

The traits which have been observed in successive generations which are unique to 'Deep Purple', either in combination, or separately are:

1. Large purple flowers.
2. Flowers positioned above or beyond the foliage.
3. Consistently double, well shaped flowers.
4. Dark green foliage, with reddish blotches on the underside.
5. Numerous flowers.
6. Upright mounded, freely branching, dense plant habit.

The new double flowered Impatiens can be compared to the Impatiens cultivar 'Burgundy Rose' (U.S. Plant Pat. No. 9,605), marketed as 'Fiesta Burgundy Rose'. In side by side comparisons, under commercial conditions, 'Deep Purple' differed from 'Burgundy Rose' as follows:

1. 'Deep Purple' tolerated higher light levels than 'Burgundy Rose'.
2. 'Deep Purple' is more vigorous and mounding than 'Burgundy Rose'.
3. Flowers of 'Deep Purple' have consistently better flower shape than 'Burgundy Rose'.
4. Flowers of 'Deep Purple' are darker and more iridescent than 'Burgundy Rose'.
5. 'Deep Purple' is more freely branching than 'Burgundy Rose'.
6. The underside of the leaves of 'Deep Purple' have reddish blotches, where the underside of the leaves of 'Burgundy Rose' is a solid green.
7. 'Deep Purple' has longer petioles, and smaller leaves than 'Burgundy Rose'.

A detailed comparison of 'Deep Purple' and 'Burgundy Rose' is set forth in Chart A at the end of the specification.

'Deep Purple' has not been observed in all possible environmental conditions. Variations in fertility, climate, light quality and/or level, soil type, and temperature may cause phenotype variations, without genotype variations.

The accompanying drawing sheets utilize color photographs to illustrate the uniqueness of the new cultivar. The coloration of the photographs may not be entirely accurate due to light reflectance, or the amount of either red or blue light captured by the film. In the event there are differences between the written description and the color in the photographs, the written description shall control.

The photograph on the first sheet depicts a side view of 'Deep Purple'. The photograph on the second sheet depicts a comparison between 'Deep Purple' and 'Burgundy Rose'. The photograph on the third sheet depicts a comparison between the flowers, stems, and foliage of 'Deep Purple' and 'Burgundy Rose'.

The following observations, measurements, values, and comparisons describe plants grown in Coquille, Oreg., under the following cultural conditions:

1. Soilless medium.
2. High nitrate fertility plus trace elements.
3. Light levels of 3,000 to 7,500 foot candles.
4. Greenhouse covering of double layer Polyethylene.
5. Day temperatures ranging from 70 F. to 85 F.
6. Night temperatures ranging from 55 F. to 60 F.
7. Four inch Azalea pots were used.
8. Comparisons were made in late October.

In the following detailed description of 'Deep Purple', all color references are made to The Royal Horticultural Society Colour Chart except where terms of ordinary usage and dictionary meaning are used.

DETAILED PLANT DESCRIPTION

Cultivar name: 'Deep Purple', marketed as 'Tioga Deep Purple'.

Botanical classification: *Impatiens walleriana.*

Parentage: Unknown.

Propagation:

*a*) *Type of cutting.*—terminal or lateral stems with leaves.

*b*) *Time to initiate roots.*—about 14 days at soil temperature of 72 F.

Roots: Numerous well branched, fibrous in type.

Plant form: Upright mounded, globular to triangular depending upon cultural practices such as pinching and fertility.

Growth habit: Vigorous, dense and bushy.

Plant height: About 20 cm.

Branching habit: Freely branching, numerous and strong. Number depends upon cultural practices, age of cuttings, and number of vegetative growth buds present on cuttings at time of propagation.

Stem: Size varies with age and cultural practices.

*a*) *Length.*—About 20 cm.

*b*) *Diameter.*—About 0.6 cm.

*c*) *Internode length.*—About 3 cm.

*d*) *Color.*—Close to 146B with 187B markings.

Foliage: Leaves are simple, generally symmetrical, abundant, alternate, and flat.

*a*) *Size of largest.*—About 3.5 cm. wide and 5 cm. long.

*b*) *Shape.*—Ovate with acuminate apex, attenuate base, and crenate margin.

*c*) *Texture.*—Smooth.

*d*) *Color.*—Abaxial or bottom — 147B with reddish blotches close to 183D.

*e*) *Color.*—Adaxial or top — 147A.

*f*) *Color.*—Abaxial or bottom venation — close to 148A.

*g*) *Color.*—Adaxial or top venation — 148A.

*h*) *Petiole.*—Length about 4.25 cm. and about 3 mm. diameter color — Close to 148A at leaf fading to 148B with reddish tinge at node end.

Flower: Large and iridescent purple in color. Consistently double and symmetrical. Freely and continuously flowering. Flower buds open similar to a rose in fullness and shape. Flowers arise from leaf node upper or outer surface. About 12 flowers and/or buds are present on each lateral stem at any given time during the flowering season. Flowers are positioned above or beyond the foliage facing upwards or outwards and are self cleaning.

*a*) *Time to flower.*—Generally four to six weeks, but can vary with age and cultural practices.

*b*) *Season.*—Year-round under greenhouse conditions. In the garden continuous from Spring through Fall.

*c*) *Flower diameter.*—About 4.25 cm.

*d*) *Flower depth.*—About 2.5 cm.

*e*) *Bud length.*—About 1 cm.

*f*) *Bud diameter.*—About 0.7 cm.

*g*) *Bud shape.*—Ovate.

*h*) *Bud color before calyx begins to open.*—145B to 145C.

*i*) *Petal/petaloids.*—Numerous — generally 25 or more. size of largest — length about 2.25 cm. and width about 2.5 cm. shape — rounded to exaggerated obovate with obtuse to emarginate apex, entire margin, cuneate to obtuse base. texture — satiny smooth.

*j*) *Petal/petaloid color.*—Iridescent purple color Adaxial surface when opening — 74A. Mature — Fade slightly, becoming less iridescent, and color measures between 74A and 74B. The outermost petals have a midline streak of 187C measuring about 1mm wide. Oldest petals/petaloids may fade to 74C to 74D or lighter, on occasion to as light as 69C to 69D in spots tending to be near the margin. Abaxial surface when opening — 71D Mature — 71D, some also have markings lighter than 69D and lighter than 157D. The outermost petal opposite the spur has a center ridge on the lower surface about 1 mm. high at base, decreasing to less than 1 mm. high at apex. The color of this ridge is close to 142A to 142B. A stripe on each side of the ridge is lighter than 157D and suffuses into 71D towards the margin.

*k*) *Spur.*—Length — about 3 cm. shape — curved acicular tube. color — close to 146D with tinges of red close to 178B at apex.

*l*) *Calyx.*—Measuring about 1 cm. wide and 1 cm. long. color — adaxial surface — close to 149D with a basal spot close to 74C to 74D. abaxial surface — close to 149D with a basal spot close to 73B. shape — ovate with cordate base, entire margin, and cuspidate apex.

*m*) *Peduncles.*—Diameter — about 2 mm. length — about 3.5 cm. strength — moderate color — 146B to 146C with reddish stripes.

*n*) *Pedicels.*—Generally 2 or 3 per peduncle diameter — between 1 and 2 mm. length — about 2.5 cm. strength — moderate color — 146B to 146C with tiny reddish stripes.

Reproductive organs: Under optimal flowering conditions, do not develop. Sterile petaloids develop in the place of the reproductive organs. 'Deep Purple' is sterile and does not produce seed.

Disease resistance: Under commercial conditions, good resistance to botrytis has been noticed.

CHART A

| | 'Deep Purple' | 'Burgundy Rose' |
|---|---|---|
| Flower | | |
| diameter | about 4.25 cm. | about 4 cm. |
| depth | about 2.5 cm. | about 1.5 cm. |
| Petal/petaloid mature color | | |
| adaxial | Between 74A and 74B | 61B |
| abaxial | 71D, some have markings lighter than 69D and lighter than 157D | 66D |
| Foliage | | |
| length | about 5 cm. | about 5.5 cm. |
| width | about 3.5 cm. | about 4.5 cm. |
| adaxial color | 147A | 147A |
| abaxial color | 147B with reddish blotches close to 183D | 147B |
| Stems | | |
| length | 20 cm. | 12 cm. |
| diameter | .6 cm. | .6 cm. |
| color | Close to 146B with 187B markings. | |
| Petiole | | |
| length | 4.25 cm. | 2.25 cm. |
| diameter | 3 mm. | 3 mm. |
| color | Close to 148A at leaf fading to 148B with reddish tinge at node end. | 144A |
| Spur | | |
| length | 3 cm. | 3 cm. |
| color | Close to 146D with tinges of red close to 178B at apex. | 146D |
| Peduncle | | |
| length | 3.5 cm. | 3 cm. |
| color | 146B to 146C with reddish stripes. | 144A |
| Pedicels | | |
| length | 2.5 cm. | 2.5 cm. |
| color | 146B to 146C with tiny reddish stripes | 144A |

It is claimed:

1. A new and distinct cultivar of double flowered Impatiens plant as herein illustrated and described.

* * * * *

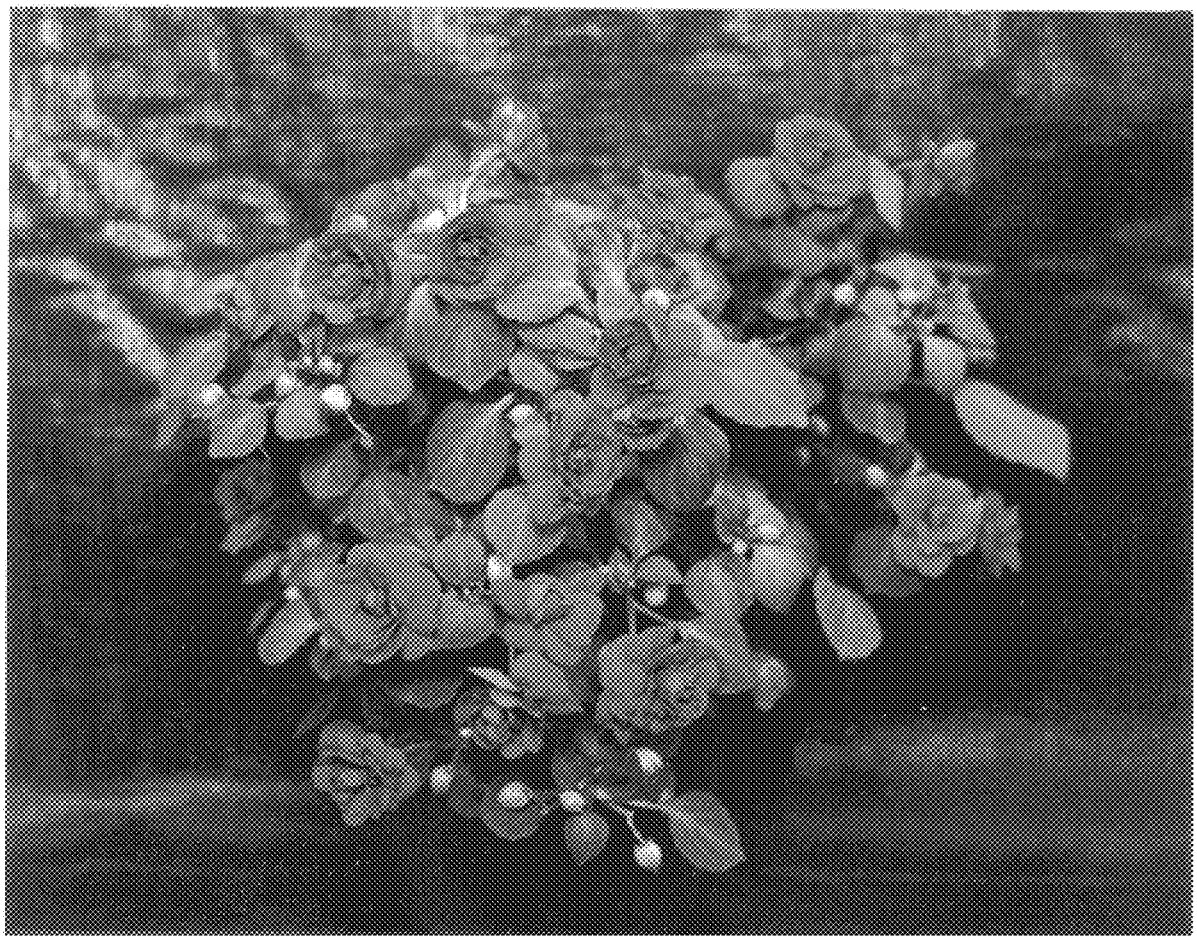

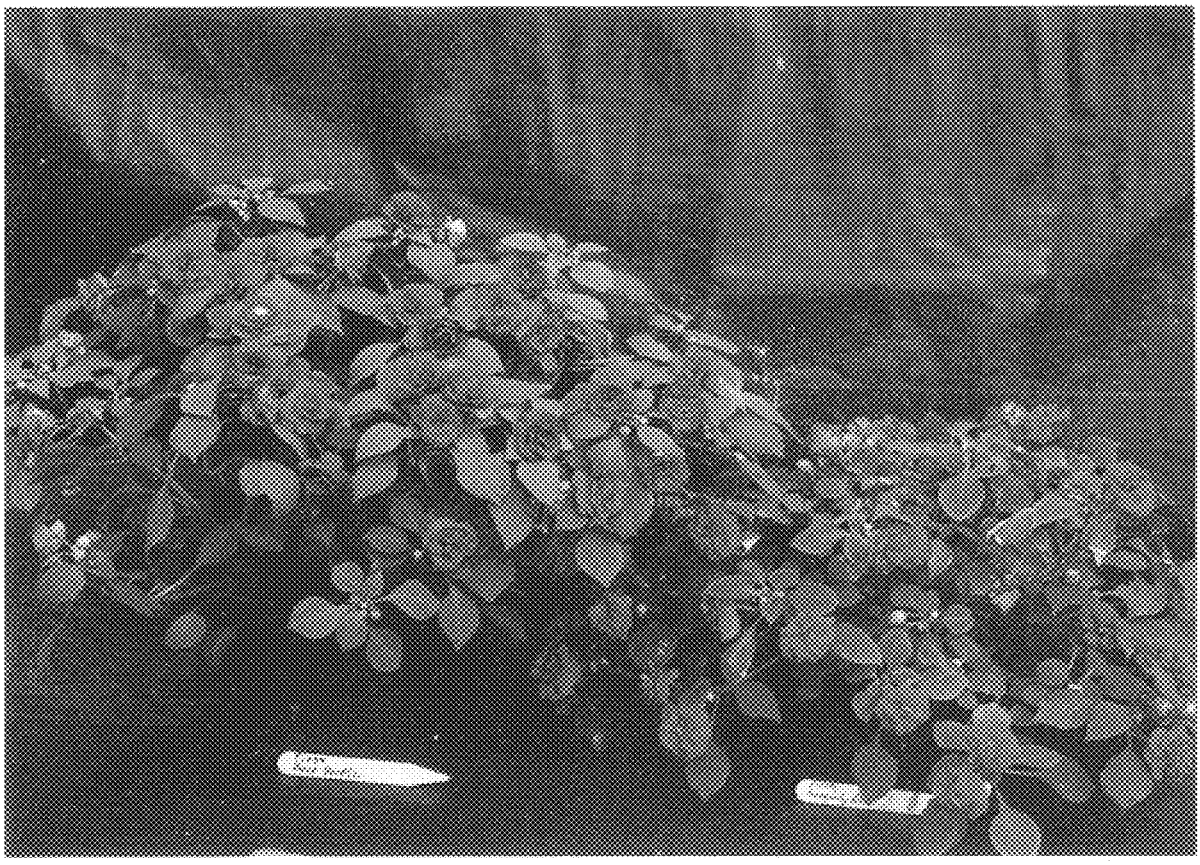

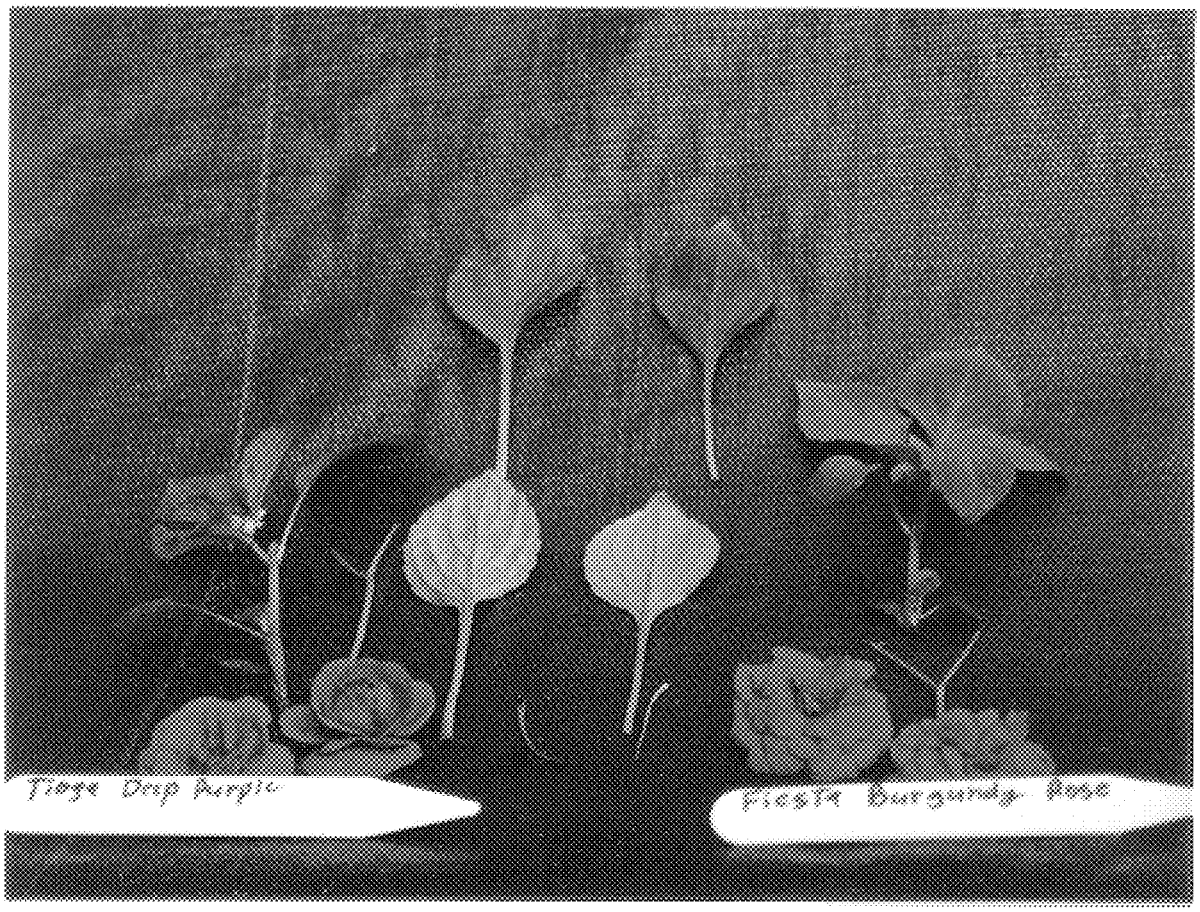
Tiger Drop Purple
Fiesta Burgundy Rose